United States Patent
Ramesh

(10) Patent No.: US 11,928,509 B2
(45) Date of Patent: Mar. 12, 2024

(54) MEMORY SYSTEM WORKLOAD ALLOCATION

(71) Applicant: Micron Technology, Inc., Boise, ID (US)

(72) Inventor: Vijay S. Ramesh, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 277 days.

(21) Appl. No.: 17/143,532

(22) Filed: Jan. 7, 2021

(65) Prior Publication Data

US 2022/0214923 A1 Jul. 7, 2022

(51) Int. Cl.
*G06K 9/00* (2022.01)
*G06F 9/50* (2006.01)
(Continued)

(52) U.S. Cl.
CPC .......... *G06F 9/5016* (2013.01); *G06T 1/0007* (2013.01); *G06T 1/60* (2013.01);
(Continued)

(58) Field of Classification Search
CPC ....... G06F 9/5016; G06T 1/60; G06T 7/0012; G06T 2210/41; G06T 2207/10081; G06T 2207/10072; G06T 2207/20081; G06T 2207/20084; G06T 2207/10088; G16H 30/20; G16H 30/40; G16H 50/20; G16H 15/00; G16H 10/60; G16H 50/70; G16H 40/67; G16H 40/20; G16H 40/63; G16H 50/30; G16H 50/50; G16H 80/00;
(Continued)

(56) References Cited

U.S. PATENT DOCUMENTS 5,322,066 A * 6/1994 Miyataka ................. G01S 7/60
600/440
6,882,864 B2 4/2005 Miyake
(Continued)

FOREIGN PATENT DOCUMENTS

EP 3706004 A1 * 9/2020 ............. G06F 12/04
KR 101656881 9/2016

OTHER PUBLICATIONS

International Search Report and Written Opinion from related PCT Application No. PCT/US2021/061443, dated Apr. 14, 2022, 10 pages.

*Primary Examiner* — Alex Kok S Liew
(74) *Attorney, Agent, or Firm* — Brooks, Cameron & Huebsch, PLLC

(57) ABSTRACT

A method includes receiving, by a processing unit coupled to a first memory device comprising a first type of media and a second memory device comprising a second type of media, data captured from an imaging device coupled to the processing unit and determining, by the processing unit, characteristics of a workload corresponding to processing of the data. The method further includes writing, by the processing unit, a portion of data associated with the workload to the other of the first memory device or the second memory device based on the determined characteristics of the workload and causing the workload to be executed while at least the portion of the data associated with the workload is written to the other of the first memory device or the second memory device.

25 Claims, 5 Drawing Sheets

(51) Int. Cl.
  *G06T 1/00* (2006.01)
  *G06T 1/60* (2006.01)
  *G06T 5/00* (2006.01)
  *G06T 7/00* (2017.01)
  *G16H 30/20* (2018.01)
  *H04M 1/725* (2021.01)

(52) U.S. Cl.
  CPC .............. *G06T 5/002* (2013.01); *G06T 5/003* (2013.01); *G06T 7/0012* (2013.01); *G16H 30/20* (2018.01); *G06T 2207/10016* (2013.01); *G06T 2207/10132* (2013.01); *H04M 1/725* (2013.01)

(58) Field of Classification Search
  CPC ........ G16H 40/60; G16H 20/40; G16H 30/00; G16H 40/40; G16H 70/20; G16H 70/60; G16H 10/65; G16H 50/80; G16H 20/60; G16H 10/40; G16H 20/17; G16H 20/70; H04M 1/72403
  USPC ........................................................ 382/128
  See application file for complete search history.

(56) References Cited

U.S. PATENT DOCUMENTS

| | | | |
|---|---|---|---|
| 7,818,521 B2 | 10/2010 | Colbey | |
| 8,427,891 B2 | 4/2013 | Best | |
| 8,886,899 B1 | 11/2014 | Bao | |
| 8,996,765 B2 | 3/2015 | Greenfield et al. | |
| 9,042,967 B2* | 5/2015 | Dacosta | A61B 5/0071 600/476 |
| 9,223,620 B2 | 12/2015 | Kim et al. | |
| 9,398,851 B2 | 7/2016 | Anand et al. | |
| 10,855,768 B2 | 12/2020 | Cooper et al. | |
| 11,275,521 B2* | 3/2022 | Christensen | G06F 3/0685 |
| 11,392,488 B2* | 7/2022 | Bergeron | G06F 12/0292 |
| 2005/0078197 A1* | 4/2005 | Gonzalez | H04N 5/772 386/E5.072 |
| 2012/0222042 A1 | 8/2012 | Chess et al. | |
| 2014/0136773 A1* | 5/2014 | Michalak | G06F 12/10 711/105 |
| 2015/0082062 A1* | 3/2015 | Saraswat | G11C 5/14 713/323 |
| 2015/0268860 A1* | 9/2015 | Yum | G06F 3/061 711/154 |
| 2015/0277793 A1* | 10/2015 | Yonezawa | G06F 12/0246 714/764 |
| 2016/0018990 A1* | 1/2016 | Yun | G06F 3/0655 711/170 |
| 2020/0286227 A1* | 9/2020 | Corredor | G06K 9/6223 |

\* cited by examiner

MEMORY SYSTEM WORKLOAD ALLOCATION

TECHNICAL FIELD

The present disclosure relates generally to semiconductor memory and methods, and more particularly, to apparatuses, systems, and methods for memory system workload allocation.

BACKGROUND

Memory devices are typically provided as internal, semiconductor, integrated circuits in computers or other electronic systems. There are many different types of memory including volatile and non-volatile memory. Volatile memory can require power to maintain its data (e.g., host data, error data, etc.) and includes random access memory (RAM), dynamic random access memory (DRAM), static random access memory (SRAM), synchronous dynamic random access memory (SDRAM), and thyristor random access memory (TRAM), among others. Non-volatile memory can provide persistent data by retaining stored data when not powered and can include NAND flash memory, NOR flash memory, and resistance variable memory such as phase change random access memory (PCRAM), resistive random access memory (RRAM), and magnetoresistive random access memory (MRAM), such as spin torque transfer random access memory (STT RAM), among others.

Memory devices may be coupled to a host (e.g., a host computing device) to store data, commands, and/or instructions for use by the host while the computer or electronic system is operating. For example, data, commands, and/or instructions can be transferred between the host and the memory device(s) during operation of a computing or other electronic system.

DETAILED DESCRIPTION

Figure 1:
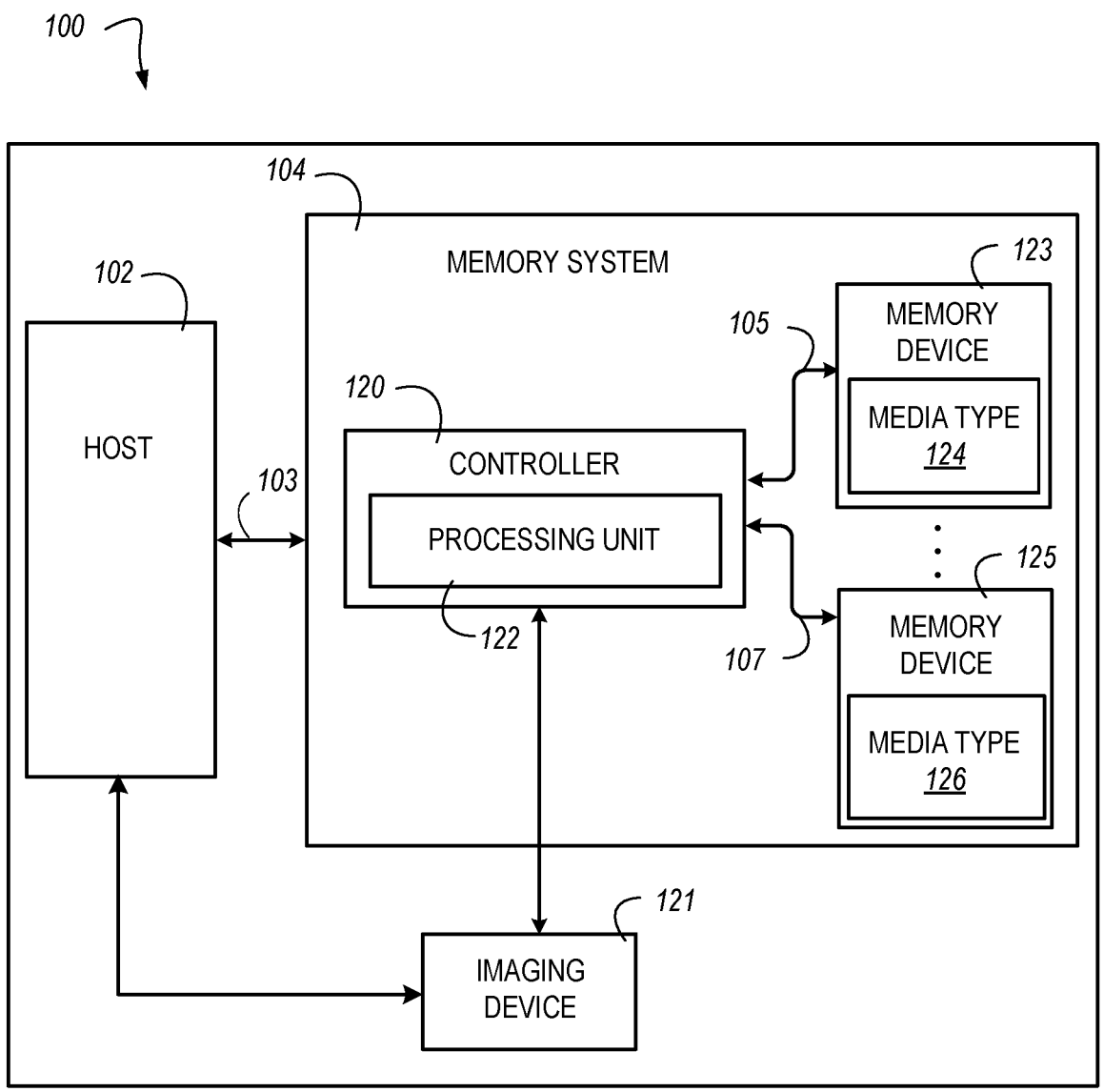
FIG. 1 is a functional block diagram in the form of an apparatus including a host and a memory device in accordance with a number of embodiments of the present disclosure.

Methods, systems, and apparatuses related to a memory system workload allocation are described. For example, data corresponding to execution of workloads executed within a memory system can be selectively written to different types of memory within the memory system. A method includes receiving, by a processing unit coupled to a first memory device comprising a first type of media and a second memory device comprising a second type of media, data captured from an imaging device coupled to the processing unit and determining, by the processing unit, characteristics of a workload corresponding to processing of the data. The method further includes writing, by the processing unit, a portion of data associated with the workload to the other of the first memory device or the second memory device based on the determined characteristics of the workload and causing the workload to be executed while at least the portion of the data associated with the workload is written to the other of the first memory device or the second memory device.

As broadband cellular network technology evolves, higher resource demands may be placed on devices connected to a broadband cellular network. This can be due to increases in available bandwidth associated with broadband cellular networks (referred to herein for brevity as "networks"), which can, in turn, give rise to higher download speeds and therefore increased data traffic associated with devices connected to the network. Such increased data traffic can further give rise a greater quantity of data be received, stored, and/or processed within devices connected to the network.

In addition, the potential for increased data traffic involving devices, such as mobile computing devices, connected to the network can allow for increasingly complicated applications (e.g., computing applications that are designed to cause a computing device to perform one or more specific functions or tasks) to be executed on the devices. Execution of such applications can in turn give rise to demanding workloads, which can strain computing resources and, more specifically, strain computing resources that are allocated in some conventional approaches.

As used herein, the term "application" generally refers to one or more computer programs that can include computing instructions that are executable to cause a computing system to perform certain tasks, functions, and/or activities. An amount of computing resources (e.g., processing resources and/or memory resources) consumed in execution of an application can be measured in terms of a "workload." As used herein, the term "workload" generally refers to the aggregate computing resources consumed in execution of applications that perform a certain task, function, and/or activity. During the course of executing an application, multiple sub-applications, sub-routines, etc. may be executed by the computing system. The amount of computing resources consumed in executing the application (including the sub-applications, sub-routines, etc.) can be referred to as the workload.

Some applications that can give rise to demanding workloads include applications that process data, such as images and/or video, in real time. Such applications, especially when processing of high-quality images and/or video in real time to correct imperfections in images and/or video are requested, can request usage of a large quantity of computing resources, and therefore create a demanding workload. Some examples of these kinds of applications can include medical diagnostic imaging applications, which can include examination of particular parts of the human body that are captured with images and/or video in real time and processed to diagnose ailments such as cataracts, cancerous cells, muscular system injuries, and/or glandular abnormalities, among others.

As workloads become increasingly demanding, especially in light of improvements to broadband cellular network technology, issues associated with optimization of workload handling can become further exacerbated in mobile computing devices (e.g., smartphones, tablets, phablets, and/or Internet-of-Things (IoT) devices, among others) where physical space constraints can dictate the amount of processing resources and/or memory resources available to the device. In addition, execution of demanding workloads using mobile computing devices can, in some approaches, quickly drain battery resources available to the mobile computing device and/or cause unwanted thermal behavior (e.g., the mobile computing device can become too hot to operate in a stable manner, etc.) for the mobile computing device. As used herein, the term "mobile computing device" generally refers to a handheld computing device that has a slate or phablet form factor. In general, a slate form factor can include a display screen that is between approximately 3 inches and 5.2 inches (measured diagonally), while a phablet form factor can include a display screen that is between approximately 5.2 inches and 7 inches (measured diagonally). Examples of "mobile computing devices" are not so limited, however, and in some embodiments, a "mobile computing device" can refer to IoT device, among other types of edge computing devices.

In order to attempt to execute demanding workloads on mobile computing devices, some approaches can include throttling performance of the mobile computing device during execution of some kinds of workloads to ensure sufficient computing resources are available to execute demanding workloads. In addition, some approaches can include throttling performance of the mobile computing device during execution of some kinds of workloads in an attempt to mitigate adverse effects on battery consumption and/or thermal behavior. However, such approaches may therefore only use a subset of the available computing resources and/or may not be able to take advantage of the available computing resources. This can be especially problematic in mobile computing devices which, as mentioned above may already feature diminished computing resources due to space constraints in comparison with, for example, a desktop computing device.

In contrast, embodiments described herein can provide hardware circuitry (e.g., a controller, processing unit, etc.) that can monitor and/or determine characteristics of workloads executed in a computing system or mobile computing device when data corresponding to the workloads is stored in different types of memory devices. The hardware circuitry can, based on the monitored or determined characteristics of the workloads, write at least a portion of the workload to a different type of memory device. For example, if the workload is executed while the data corresponding to the workload is stored in a volatile memory device and the hardware circuitry determines that execution of the workload can be optimized if the data corresponding to the workload is stored in a non-volatile memory device, the hardware circuitry can cause at least a portion of the data corresponding to the workload to be written to the non-volatile memory device. Such dynamic determination of workload characteristics and subsequent allocation of workloads to memory devices that include different types of media can be especially beneficial in mobile computing systems, especially as increasingly processing resource intensive workloads are executed on mobile computing devices.

Non-limiting examples of how the workload can be optimized can include optimizing battery consumption of the computing system, bandwidth associated with the computing system, computing resource consumption associated with the computing system, and/or speed of execution of the workload by the computing system, among others. For example, if the computing system is a mobile computing device (e.g. a smartphone, IoT device, etc.), battery power of the computing device may be rapidly depleted when the workload is executed involving certain types of high power consumption memory devices. Accordingly, in order to optimize battery power consumption, for example of a mobile computing device, the hardware circuitry can cause at least a portion of the data corresponding to the workload to be written to a memory device that is characterized by a lower power consumption in executing the workload.

Another non-limiting example of the workload can be optimized can include optimizing execution of the workload by utilizing memory devices and/or media types that exhibit different memory capacities versus bandwidth capabilities. For example, a memory device that exhibits high capacity but low bandwidth (e.g., a NAND memory device) can be utilized for execution of some types of workloads (or portions thereof) while a memory device that exhibits high bandwidth but low capacity (e.g., a 3D stacked SDRAM memory device) can be utilized for execution of some types of workloads (or portions thereof). By leveraging the capacity of a memory device that exhibits high capacity but low bandwidth, or vice versa, for differing workloads, embodiments herein can optimize an amount of time, processing resources, and/or power consumed in executing resource intensive applications in a computing device or mobile computing device. Embodiments are not so limited, however, and other examples of optimizing execution of the workload in accordance with the disclosure are described in more detail, herein.

As described in more detail, herein, embodiments can further optimize execution of workloads in mobile computing system by writing data associated with the workloads to the memory devices based on characteristics of that data such as access frequencies of data involved in execution of the workloads. Access frequency of the data can refer to a quantity of accesses (e.g., reads, writes, etc.) involving the data in execution of the workloads. Access frequency of the data can be referred to herein in terms of "hot data" and "cold data." "Cold data," as used herein, means that a particular memory object has not been accessed for a long duration relative to other memory objects read from a memory device. "Hot data," as used herein, means that a particular memory object has been accessed frequently relative to other memory objects read from a memory device.

For example, if certain data involved in execution of a workload is determined to be "hot," such data can be written to a memory device that includes a media type that is well suited for making data quickly accessible. A non-limiting example of a memory device to which hot data can be written during execution of the workloads described herein is a volatile memory device such as a DRAM device.

In contrast, if certain data involved in execution of a workload is determined to be "cold," such data can be written to a memory device that includes a media type that is well suited for storing data that is not frequently accessed. A non-limiting example of a memory device to which cold data can be written during execution of the workloads described herein is a non-volatile memory device such as a NAND flash device.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

As used herein, designators such as "N," "M," etc., particularly with respect to reference numerals in the drawings, indicate that a number of the particular feature so designated can be included. It is also to be understood that the terminology used herein is for the purpose of describing particular embodiments only, and is not intended to be limiting. As used herein, the singular forms "a," "an," and "the" can include both singular and plural referents, unless the context clearly dictates otherwise. In addition, "a number of," "at least one," and "one or more" (e.g., a number of memory banks) can refer to one or more memory banks, whereas a "plurality of" is intended to refer to more than one of such things.

Furthermore, the words "can" and "may" are used throughout this application in a permissive sense (i.e., having the potential to, being able to), not in a mandatory sense (i.e., must). The term "include," and derivations thereof, means "including, but not limited to." The terms "coupled" and "coupling" mean to be directly or indirectly connected physically or for access to and movement (transmission) of commands and/or data, as appropriate to the context. The terms "data" and "data values" are used interchangeably herein and can have the same meaning, as appropriate to the context.

The figures herein follow a numbering convention in which the first digit or digits correspond to the figure number and the remaining digits identify an element or component in the figure. Similar elements or components between different figures may be identified by the use of similar digits. For example, 104 may reference element "04" in FIG. 1, and a similar element may be referenced as 204 in FIG. 2. A group or plurality of similar elements or components may generally be referred to herein with a single element number. For example, a plurality of reference elements, e.g., elements 126-1 to 126-N (or, in the alternative, 126-1, . . . 126-N) may be referred to generally as 126. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 is a functional block diagram in the form of a computing system 100 including an apparatus including a host 102 and a memory system 104 in accordance with a number of embodiments of the present disclosure. As used herein, an "apparatus" can refer to, but is not limited to, any of a variety of structures or combinations of structures, such as a circuit or circuitry, a die or dice, a module or modules, a device or devices, or a system or systems, for example. In some embodiments, the computing system 100 can be a mobile computing system (e.g., a mobile computing device, such as the mobile computing device 501 illustrated in FIG. 5, which can be a smartphone, a tablet, a phablet, and/or a IoT device, among others). The memory system 104 can include a number of different memory devices 123, 125 (and/or 227 illustrated in FIG. 2, herein), which can include one or more different media types 123, 125 (and/or 227 illustrated in FIG. 2, herein). The different memory devices 123, 125, and/or 227 can include one or more memory modules (e.g., single in-line memory modules, dual in-line memory modules, etc.).

The memory system 104 can include volatile memory and/or non-volatile memory. In a number of embodiments, memory system 104 can include a multi-chip device. A multi-chip device can include a number of different memory devices 123, 125, and/or 227, which can include a number of different memory types and/or memory modules. For example, a memory system can include non-volatile or volatile memory on any type of a module. As shown in FIG. 1, the computing system 100 can include a controller 120, which can include a processing unit 122. Each of the components (e.g., the host 102, the controller 120, the processing unit 122, and/or the memory devices 123, 125 can be separately referred to herein as an "apparatus."

The memory system 104 can provide main memory for the computing system 100 or could be used as additional memory and/or storage throughout the computing system 100. The memory system 104 can include one or more memory devices 123, 125, which can include volatile and/or non-volatile memory cells. At least one of the memory devices 123, 125 can be a flash array with a NAND architecture, for example. Further, at least one of the memory devices 123, 125 can be a dynamic random-access array of memory cells. Embodiments are not limited to a particular type of memory device. For instance, the memory system 104 can include RAM, ROM, DRAM, SDRAM, PCRAM, RRAM, and/or flash memory (e.g., NAND and/or NOR flash memory devices), among others.

Embodiments are not so limited, however, and the memory system 104 can include other non-volatile memory devices 123, 125 such as non-volatile random-access memory devices (e.g., NVRAM, ReRAM, FeRAM, MRAM, PCM), "emerging" memory devices such as resistance variable (e.g., 3-D Crosspoint (3D XP)) memory devices, memory devices that include an array of self-selecting memory (SSM) cells, etc., or any combination thereof.

Resistance variable memory devices can perform bit storage based on a change of bulk resistance, in conjunction with a stackable cross-gridded data access array. Additionally, in contrast to many flash-based memories, resistance variable non-volatile memory can perform a write in-place operation, where a non-volatile memory cell can be programmed without the non-volatile memory cell being previously erased. In contrast to flash-based memories and resistance variable memories, self-selecting memory cells can include memory cells that have a single chalcogenide material that serves as both the switch and storage element for the memory cell.

As shown in FIG. 1, the memory devices 123, 125 include different types of memory devices. For example, the memory device 125 can be a 3D XP memory device or a NAND memory device, among others, and the memory device 123 can be a volatile memory device, such as a DRAM device, or vice versa. That is, the memory devices 123, 125 can include different media types 124, 126. Embodiments are not so limited, however, and the memory devices 123, 125 can include any type of memory devices provided that at least two of the memory devices 123, 125 include different media types 124, 126. As used herein, a "media type" generally refers to a type of memory cell architecture that corresponds to the memory devices 123, 125. For example, one of the media types 124, 126 can correspond to an array of memory cells that include at least one capacitor and at least one transistor, while another of the media types 124, 126 can include an array of floating-gate metal-oxide-semiconductor field-effect transistors. In some embodiments, at least one of the media types 124, 126 can include an array of resistance variable memory cells that are configured to perform bit storage based on a change in a bulk resistance associated with the resistance variable memory cells.

As illustrated in FIG. 1, a host 102 can be coupled to the memory system 104. In a number of embodiments, the memory system 104 can be coupled to the host 102 via one or more channels (e.g., channel 103). In FIG. 1, the memory system 104 is coupled to the host 102 via channel 103, which can, in addition, be coupled to the controller 120 and/or the processing unit 122 of the memory system 104. The controller 120 and/or the processing unit 122 are coupled to the memory devices 123, 125 via channel(s) 105, 107. In some embodiments, each of the memory devices 123, 125 are coupled to the controller 120 and/or the processing unit 122 by one or more respective channels 105, 107 such that each of the memory devices 123, 125 can receive messages, commands, requests, protocols, or other signaling that is compliant with the type of memory device 123, 125 (e.g., messages, commands, requests, protocols, or other signaling that is compliant with the media type 124, 126 of the memory devices 123, 125) coupled to the controller 120.

The computing system 100 can further include an imaging device 121. The imaging device 121 can be communicatively coupled to the host 102 and/or to the memory device 104 (e.g., to the controller 120 and/or the processing unit 122). The imaging device 121 can be a camera, sonography device, ultrasound device, stereoscopic imaging device, magnetic resonance imaging device, infrared imaging device, or other imaging device that can capture data that includes images or streams of images (e.g., streaming video and/or "live-streaming video") in real-time and transmit information corresponding to the images and/or streams of images to the computing system 100. In general, the imagining device can be any mechanical, digital, or electronic viewing device; still camera; camcorder; motion picture camera; or any other instrument, equipment, or format capable of recording, storing, or transmitting images, video, and/or information.

As used herein, the term "live-streaming video," and variants thereof, generally refers to sequences of images that are concurrently (or nearly concurrently) captured and processed, reproduced, and/or broadcasted. In some embodiments, "live-streaming" video can be referred to in the alternative herein as "data captured by an imaging device" or "data captured from an imaging device." Further, as used herein, the term "streaming video," and variants thereof generally refers to sequences of images that are captured by an imaging device and subsequently processed, reproduced, and/or broadcasted. In some embodiments, "streaming" video can be referred to in the alternative herein as "data captured by an imaging device" or "data captured from an imaging device."

Generally, such data (e.g., images, streams of images and/or or "live-streaming" video) captured by the imaging device can be displayed or broadcast on a viewing device and/or processed by a processing unit within a threshold period of time after capture by the imaging device. In some embodiments, the data captured by the imaging device can be displayed, broadcast, and/or processed within a threshold period of time relative to capture of the imaging device that is on the order of seconds or minutes, as opposed to hours or days. These data (e.g., streams of images and/or video) can include any media content live or recorded that is delivered to or by a computing system, such as a mobile computing device, via a connection path, such as a wired communication channel, and/or a non-wired communication channel such as the internet and displayed or broadcast in real time. Accordingly, as described in more detail herein, data can be captured by an imaging device and then stored in memory coupled to the imaging device, processed by a processing unit associated with the memory device, and subsequently broadcast and/or the data can be captured by the imaging device, stored in memory coupled to the imaging device, processed by a processing unit associated with the memory device, and/or broadcast in real-time (or near real-time based on latencies in transmission between various components described herein) as the data is captured by the imaging device.

In some embodiments, the imaging device 121 can capture data, such as images and/or streaming video (e.g., live-streaming video) that includes images used in a medical self-diagnostic test. As used herein, a "medical self-diagnostic test" generally refers to medical testing performed by a patient from a location different than a doctor's office, clinic, hospital, or other health care service location. In general, a medical self-diagnostic test is performed by a patient using equipment that is owned by the patient and is commonly not medical grade equipment. For example, embodiments herein described the use of a smartphone or other mobile computing device in performance of a medical self-diagnostic test.

In some embodiments, the images and/or streaming video captured by the imaging device 121 can include images and/or streaming video of an eyeball, an ear canal, a nasal passage, a uterus, and/or a testicle, among others. Such images and/or streaming video can be captured by the imaging device 121 and processed locally within the memory system 104 as part of a medical self-diagnostic test. By utilizing such aspects of the disclosure, medical self-diagnostic tests can be performed in the absence of a visit to a doctor or hospital, which can alleviate wait times for medical patients and/or can preemptively capture medical information for a medical professional to view at a later time. In addition, such medical self-diagnostic tests can provide information over time in the absence of doctor office visits that can be amalgamated over time to assist in early detection of medical issues and/or to generate a consistent record of medical abnormalities that can later be analyzed by a doctor or other clinical professional.

For example, ultrasound images and/or video of a fetus can be captured by the imaging device 121 and processed by the memory system 104 to ensure healthy growth of the fetus and/or to detect and identify potential abnormalities in the fetus during a pregnancy in the absence of visits to a doctors' office or hospital. Further, early signs of testicular abnormalities (e.g., signs of testicular cancer or other ailments involving the testes) and/or ocular abnormalities (e.g., cataracts or other ailments involving the eyes) can be captured by the imaging device 121 and processed by the memory system 104 to assist with early detection of such abnormalities in the absence of visits to a doctors' office or hospital. Other examples of potential abnormalities that can be uncovered in accordance with the disclosure include abnormalities of the ears, nose, throat, glands, joints, and/or muscles, among others.

Traditionally, capture and processing/analysis of such medical abnormalities is a highly specialized and computing resource intensive process. For example, applications and hence, the workloads corresponding thereto, to perform medical imaging and/or process medical imaging data can be extremely computing resource intensive. One reason for this is that the level of detail captured in images or video for medical imaging purposes is often times extremely detailed and therefore memory resource intensive (e.g., because of the detail captured in such images and/or videos, the file sizes corresponding to the images and/or videos can be relatively large in comparison to, for example, a simple photograph). Another reason for the resource intensive nature of execution of applications and corresponding workloads to process medical imaging data is that the detail and size of the data (e.g., the file sizes associated with medical imaging data) can require multiple resource intensive operations in processing.

However, embodiments herein can allow for selective processing of workloads involving images and/or video corresponding to the images and/or video captured by the imaging device 121 such that the workloads corresponding to execution of applications involving the same are allocated to the memory devices 123, 125, 227 to optimize the performance of the memory system 104 such that the medical self-diagnostic tests described herein can be realized using a mobile computing device, such as a smartphone, among other mobile computing devices described herein.

In some embodiments, the images and/or video captured by the imaging device 121 and processed by the memory system 104 can be uploaded or otherwise transferred to a medical professional to assist in building long term records of the development of potential medical abnormalities and providing notifications of these records to a medical professional even if a patient is remiss in visiting a doctor or hospital regularly.

The host 102 can be a host system such as a personal laptop computer, a desktop computer, a digital camera, a smart phone, a memory card reader, and/or an internet-of-things (IoT) enabled device, among various other types of hosts. In some embodiments, however, the host 102 is a mobile computing device such as a digital camera, a smart phone, a memory card reader, and/or an internet-of-things (IoT) enabled device, among various other types of hosts (e.g., in some embodiments, the host 102 is not a personal laptop computer or desktop computer). The host 102 can include a system motherboard and/or backplane and can include a memory access device, e.g., a processor (or processing device).

One of ordinary skill in the art will appreciate that "a processor" can intend one or more processors, such as a parallel processing system, a number of coprocessors, etc. The system 100 can include separate integrated circuits or one or more of the host 102, the memory system 104, the control circuitry 120, and/or the memory devices 126-1 to 126-N can be on the same integrated circuit. The computing system 100 can be, for instance, a server system and/or a high-performance computing (HPC) system and/or a portion thereof. Although the example shown in FIG. 1 illustrate a system having a Von Neumann architecture, embodiments of the present disclosure can be implemented in non-Von Neumann architectures, which may not include one or more components (e.g., CPU, ALU, etc.) often associated with a Von Neumann architecture.

The memory system 104 can include a controller 120, which can include a processing unit 122. The processing unit 122 can be provided in the form of an integrated circuit, such as an application-specific integrated circuit (ASIC), field programmable gate array (FPGA), reduced instruction set computing device (RISC), advanced RISC machine, system-on-a-chip, or other combination of hardware and/or circuitry that is configured to perform operations described in more detail, herein. In some embodiments, the processing unit 122 can comprise one or more processors (e.g., processing device(s), co-processors, etc.)

The processing unit 122 can perform operations to monitor and/or determine characteristics of workloads running on the memory system 104. The characteristics can include information such as bandwidth consumption, memory resource consumption, access frequency (e.g., whether the data is hot or cold), and/or power consumption in execution of the workloads, among others. The processing unit 122 can control writing of at least a portion of the data to a different memory device 123, 125 in order to optimize execution of the workload, balance the workload between different memory devices 123, 125 for media management purposes, and/or optimize battery consumption of the computing system 100, among others.

In a non-limiting example, an apparatus (e.g., the computing system 100) can include a first memory device 123 comprising a first type of media 124 and a second memory device 125 comprising a second type of media 126. The first memory device 123, the second memory device 125, and the processing unit 122 can, in some embodiments, be resident on a mobile computing device (e.g., the mobile computing device 501 illustrated in FIG. 5, herein) such as a smartphone. A processing unit 122 can be coupled to the first memory device 123 and the second memory device 125. The processing unit 122 can receive information captured by an imaging device 121 couplable to the processing unit 122.

As used herein, the term "resident on" refers to something that is physically located on a particular component. For example, the first memory device 123, the second memory device 125, and/or the processing unit 122 can, in some embodiments, being resident on a smartphone (e.g., the computing device 100 and/or the mobile computing device 501 illustrated in FIG. 5, herein) refers to a condition in which the first memory device 123, the second memory device 125, and/or the processing unit 122 is physically coupled to, or physically within, smartphone (e.g., the computing device 100 and/or the mobile computing device 501 illustrated in FIG. 5, herein). The term "resident on" may be used interchangeably with other terms such as "deployed on" or "located on," herein.

The processing unit 122 can execute an operation to process the received information captured by the imaging device 121. In some embodiments, the operation to process received information captured by the imaging device 121 can involve an application having a particular workload corresponding thereto. The processing unit 122 can determine characteristics of the workload when the workload is written to the first memory device 123 or the second memory device 125. In some embodiments, the characteristics of the workload can include at least one of an access frequency of data associated with the workload, a latency associated with execution of the workload, and/or an amount of processing resources consumed in execution of the workload. In some embodiments, the application and/or the workload can involve processing of data received and/or captured by the imaging device 121.

The processing unit 122 can determine, based on the characteristics of the workload, whether to write at least a portion of data associated with the workload to the other of the first memory device 123 or the second memory device 125 and control allocation of execution of the workload that is written to the other of the first memory device 123 or the second memory device 125 such that at least the portion of the workload is subsequently executed after at least the portion of the workload has been written to the other of the first memory device 123 or the second memory device 125. In some embodiments, the subsequently executed workload can involve processing of data received and/or captured by the imaging device 121.

In some embodiments, the processing unit 122 can determine that the workload corresponds to performance of an ultrasound imaging operation, as described in more detail in connection with FIG. 5, herein. The processing unit 122 can then receive, from the imaging device 121, information that corresponds to the ultrasound imaging operation and write the information that corresponds to the ultrasound imaging operation to the first memory device 123 or the second memory device 125 based, at least in part on the determination that the workload corresponds to performance of the ultrasound imaging operation. In some embodiments, the information that corresponds to the ultrasound imaging operation can be received and/or captured by the imaging device 121.

Continuing with the above non-limiting example, the processing unit 122 can determine that the workload corresponds to performance of an operation to detect an abnormality in at least one of an eyeball, an ear, a nose, or a testicle, or any combination thereof, as described in more detail in connection with FIG. 5, herein. The processing unit 122 can then receive, from the imaging device 121, information that corresponds to the detected abnormality in at least the one the eyeball, the ear, the nose, and/or the testicle and write at least the portion of the data associated with the workload to the other of the first memory device 123 or the second memory device 125 based, at least in part, on the determination that the workload corresponds to performance of the operation to detect the abnormality in at least one of the eyeball, the ear, the nose, or the testicle.

In some embodiments, the processing unit 122 can determine that the workload corresponds to performance of an operation to process an image or a video received from the imaging device 121. The processing unit 122 can then write at least the portion of the data associated with the workload to the other of the first memory device 123 or the second memory device 125 based, at least in part, on the determination that the workload corresponds to performance of the operation to process the image or the video received from the imaging device 121 and cause performance of the operation to process the image or the video by replacing at least one pixel of the image or the video, correcting a blurred portion of the image or the video, or removing noise from the image and/or the video. For example, in the process of image capture, one or more pixels of an image or video may become corrupted, which can cause the image to be distorted, blurred, or include other types of noise. By performing operations to replace the corrupted portions (e.g., pixels) of the image, the image or video quality can be recovered and/or improved using circuitry that is entirely resident on the memory system (e.g., in the absence of transferring the images and/or video to external circuitry, such as the host 102). In some embodiments, the image and/or the video can be received from the imaging device 121 and processed in a live-streaming manner. For example, the video can be a live video captured in real-time by the imaging device 121 and written in real time to the memory system 104.

As mentioned above, the first memory device 123 or the second memory device 125 can be a non-persistent (e.g., volatile) memory device, and the other of the first memory device 123 or the second memory device 125 can be a persistent (e.g., non-volatile) memory device. In addition, as mentioned above, in some embodiments, the first type of memory or the second type of memory, or both, comprises sets of memory cells that exhibit different storage characteristics. For example, the first memory device 123 can have a first media type 124 and the second memory device 125 can have a second media type 126 associated therewith.

Figure 3:
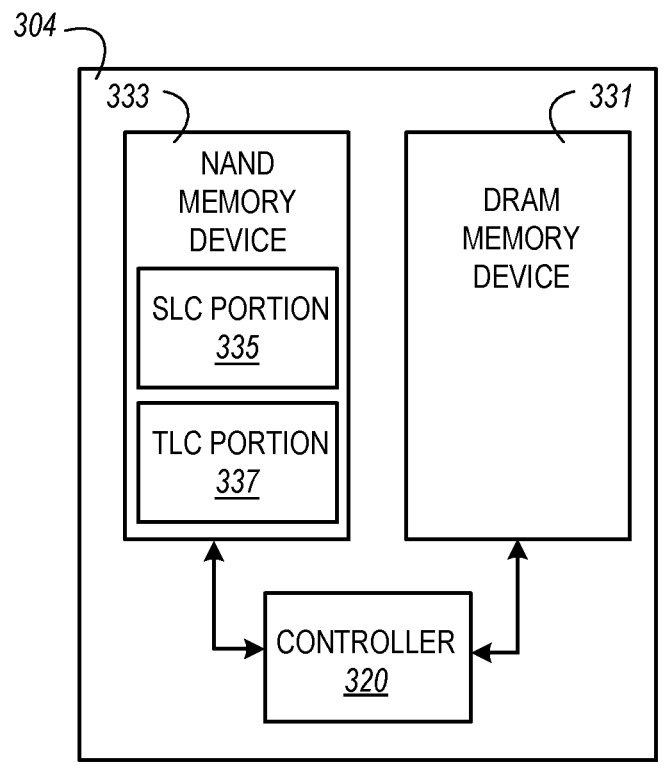
FIG. 3 is a functional block diagram in the form of an apparatus including a memory system in accordance with a number of embodiments of the present disclosure.
Figure 4:
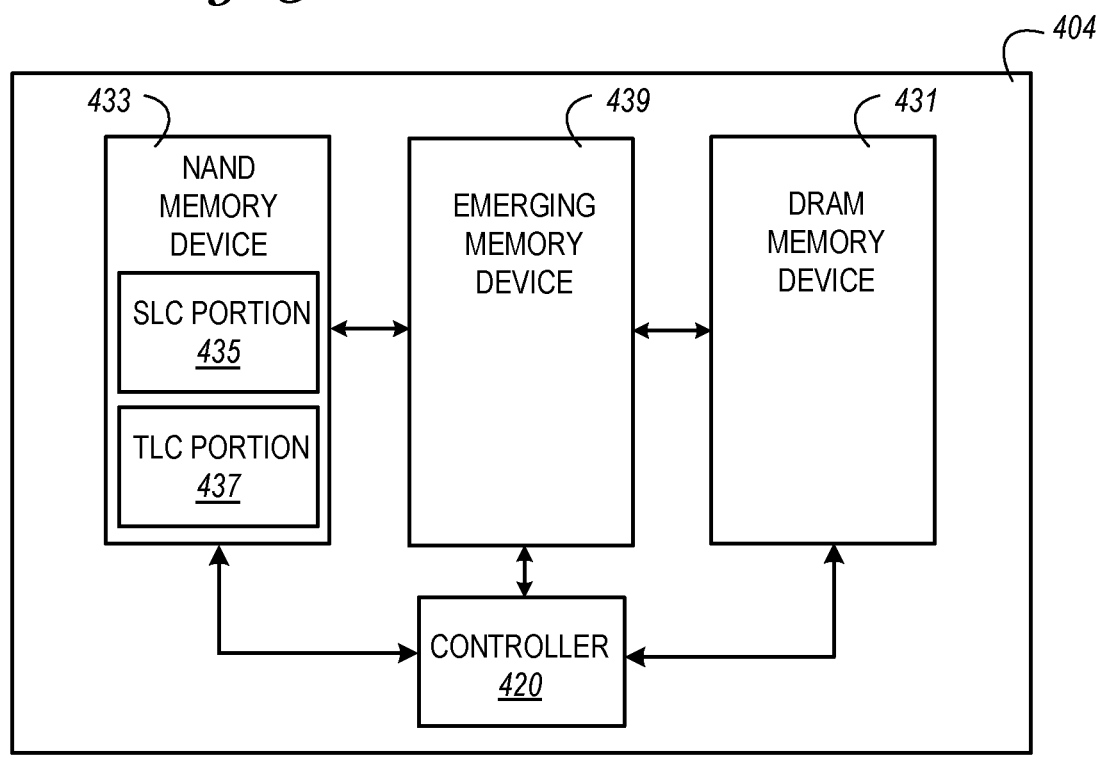
FIG. 4 is another functional block diagram in the form of an apparatus including a memory system in accordance with a number of embodiments of the present disclosure.

Continuing with the above non-limiting example, the first memory device 123 or the second memory device 125 can be a NAND flash memory device that comprises a set of single level memory cells (SLCs) and a set of multi-level memory cells (MLCs), as shown in FIGS. 3 and 4, herein. In such embodiments, the processing unit 122 can write at least the portion of the data associated with the workload to the set of SLC memory cells or the set of MLC memory cells based, at least in part, on the characteristics of the workload. In some embodiments, the set of SLCs can be configured to store a look-up table to facilitate writing of at least the portion of the data to the other of the first memory device 123 or the second memory device 125.

As used herein, the term "look-up table" generally refers to a data structure that contains indexing information that can correspond to desired output formats of data written to the memory system 104. For example, the look-up table can include pre-fetched information that can be used by the memory system 104 to output various types of data processed by the memory system in a requested format. In some embodiments, the look-up table can be included in a flash memory device, such as the NAND memory device 333, for example, in the SLC portion 335 of the NAND memory device 333. The look-up table can store data corresponding to artificial intelligence and/or machine learning applications. In such embodiments, it may be beneficial to store the look-up table in a SLC portion of the memory device, as SLC memory generally offers high access speeds and accurate storage. In some embodiments, such artificial intelligence and/or machine learning applications can be executed in connection with performance of the operations described herein.

The embodiment of FIG. 1 can include additional circuitry that is not illustrated so as not to obscure embodiments of the present disclosure. For example, the memory system 104 can include address circuitry to latch address signals provided over I/O connections through I/O circuitry. Address signals can be received and decoded by a row decoder and a column decoder to access the memory system 104 and/or the memory devices 123, 125. It will be appreciated by those skilled in the art that the number of address input connections can depend on the density and architecture of the memory system 104 and/or the memory devices 123, 125.

Figure 2:
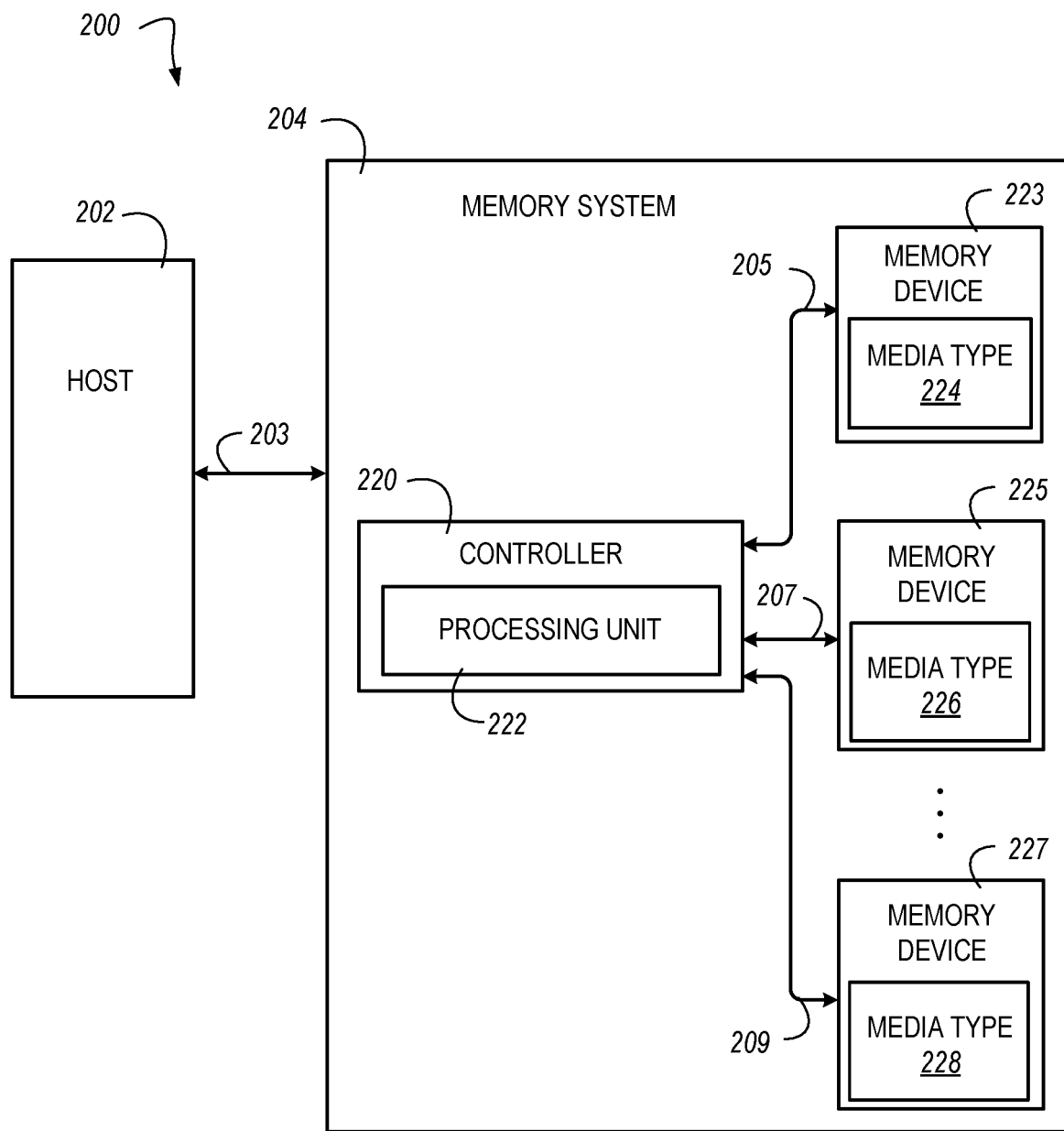
FIG. 2 is another functional block diagram in the form of a computing system including an apparatus including a host and a memory system in accordance with a number of embodiments of the present disclosure.

FIG. 2 is another functional block diagram in the form of a computing system 200 including an apparatus including a host 202 and a memory system 204 in accordance with a number of embodiments of the present disclosure. In some embodiments, the computing system 200 can be a mobile computing system (e.g., a mobile computing device 501, such as a smartphone, a tablet, a phablet, and/or a IoT device, among others). The memory system 204 can include a number of different memory devices 223, 225, 227, which can include one or more different media types 223, 225, 227. The different memory devices 223, 225, and/or 227 can include one or more memory modules (e.g., single in-line memory modules, dual in-line memory modules, etc.). The host 202, memory system 204, controller 220, processing unit 222, memory devices 223, 225 and/or the media types 224, 226 can be analogous to the host 102, memory system 104, controller 120, processing unit 122, memory devices 123, 125 and/or the media types 124, 126 illustrated in FIG. 1, herein.

In some embodiments, each of the memory devices 223, 225, and 227 can be different types of memory devices. Accordingly, in some embodiments, each of the memory devices 223, 225, and 227 can include different media types 224, 226, and 228. In a non-limiting example, the memory device 223 can be a volatile memory device, such as a DRAM device and can include a media type 224 that corresponds to a DRAM memory device (e.g., an array of memory cells that include at least one capacitor and at least one transistor). Continuing with this example, the memory device 225 can be a flash memory device, such as a NAND memory device and can include a media type 226 that corresponds to a NAND memory device (e.g., comprises an array of floating-gate metal-oxide-semiconductor field-effect transistors). In this non-limiting example, the memory device 227 can be an emerging memory device (e.g., the emerging memory device 439 illustrated in FIG. 4, herein), such as the emerging memory devices described above, and can include a media type 228 that corresponds to an emerging memory device (e.g., an array of resistance variable memory cells that are configured to perform bit storage based on a change in a bulk resistance associated with the resistance variable memory cells).

The memory devices 223, 225, and 227 can be configured to read, write, and/or store data corresponding to one or more workloads executed by the computing system 200. An application corresponding to the workload can be executed by, for example, the processing unit 222 to cause the data written to the memory devices 223, 225, and 227 to be used in execution of the application and/o workload. As described above, the controller 220 can control writing at least a portion of the data to a different memory device than the memory device in which the data is initially written based on characteristics of the workload.

For example, if data corresponding to a particular workload is stored in the memory device 223, the controller 220 and/or the processing unit 222 can, in response to a determination that the workload may be more efficiently executed (e.g., optimized) using a different memory device, cause at least a portion of the data corresponding to the particular workload to be written to the memory device 225 and/or to the memory device 227.

Figure 5:
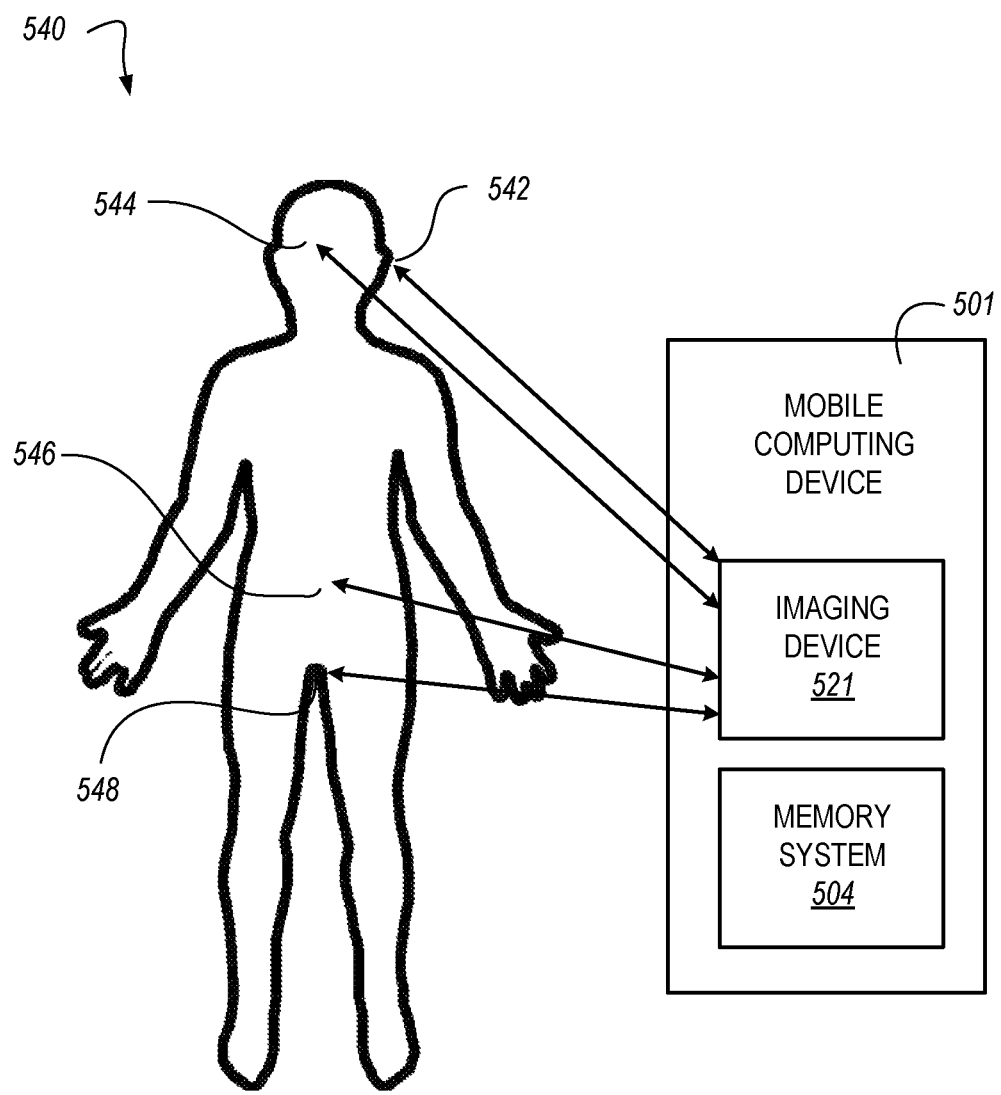
FIG. 5 is a diagram illustrating a human medical self-diagnostic test subject and a mobile computing device in accordance with a number of embodiments of the present disclosure.

In a non-limiting example, a system (e.g., the computing system 200 and/or the mobile computing device 501 illustrated in FIG. 5, herein) can include a memory system 204 comprising a processing unit 222, a first memory device 223 comprising a first type of media 224, a second memory device 225 comprising a second type of media 226, and a third memory device 227 comprising a third type of media 228. In some embodiments, the first memory device 223 can be a dynamic random-access memory device, the second memory device 225 can be a NAND flash memory device, and the third memory device 227 can be an emerging memory device, such as a 3D XP memory device, a self-selecting cell memory device, etc., as described above.

In at least one embodiment, the media type 224 comprises an array of memory cells that include at least one capacitor and at least one transistor, the media type 226 comprises an array of floating-gate metal-oxide-semiconductor field-effect transistors, and the type of media 228 comprises an array of resistance variable memory cells that are configured to perform bit storage based on a change in a bulk resistance associated with the resistance variable memory cells.

An imaging device (e.g., the imaging device 121 illustrated in FIG. 1, herein) can be coupled to the memory device 204. In such examples, the processing unit 222 can receive signaling comprising information captured by the imaging device and execute, using data written to the memory device 223, the memory device 225, or the memory device 227, a workload that includes processing the information detected by the imaging device. As discussed herein, the memory system 204 and the imaging device can be resident on a mobile computing device (e.g., the computing system 200 and/or the mobile computing device 501 illustrated in FIG. 5, herein).

The processing unit 222 can determine characteristics of the executed workload while the data is written to the memory device 223, the memory device 225, or the memory device 227 and write at least a portion of data associated with the workload to at least one of the other of the memory device 223, the memory device 225, or the memory device based 227, at least on part, on the determined characteristics of the workload and the information detected by the imaging device.

In some embodiments, the processing unit 222 can write at least the portion of data associated with the workload to at the least one of the other of the memory device 223, the memory device 225, or the memory device 227 to optimize battery consumption of the mobile computing device as part of execution of the workload that includes processing the information detected by the imaging device.

As described herein, the memory system 204 and the imaging device can be resident on a mobile computing device and the processing unit 222 can receive data (e.g., images, streams of images, and/or live-streaming information) from the imaging device in conjunction with performance of a medical self-diagnostic test and the processing unit 222 can write at least a portion of the data from the imaging device to at least one of the other of the memory device 223, the memory device 225, or the memory device based 227, at least on part, on a determined category associated with the medical self-diagnostic test. In this example, the processing unit 222 can execute, using at least the portion of the data captured by the imaging device written to the memory device 223, the memory device 225, or the memory device 227, a workload that includes at least the portion of the data captured from the imaging device.

In such examples, the processing unit 222 can determine the characteristics of the executed workload while the data is written to the memory device 223, the memory device 225, or the memory device 227 by monitoring at least one of an access frequency of data associated with the workload, a latency associated with execution of the workload, and/or an amount of processing resources consumed in execution of the workload and write at least the portion of data associated with the workload to at least one of the other of the memory device 223, the memory device 225, or the memory device 227 based, at least on part, on the determined access frequency of data associated with the workload, the latency associated with execution of the workload, and/or the amount of processing resources consumed in execution of the workload.

In some embodiments, at least a portion of the data written to the memory device 223, the memory device 225, or the memory device 227 is formatted according to a universal number format or a posit format. In contrast to the IEEE 754 floating-point or fixed-point binary formats, which include a sign bit sub-set, a mantissa bit sub-set, and an exponent bit sub-set, universal number formats, such as posits include a sign bit sub-set, a regime bit sub-set, a mantissa bit sub-set, and an exponent bit sub-set. This can allow for the accuracy, precision, and/or the dynamic range of a posit to be greater than that of a float, or other numerical formats. In addition, posits can reduce or eliminate the overflow, underflow, NaN, and/or other corner cases that are associated with floats and other numerical formats. Further, the use of posits can allow for a numerical value (e.g., a number) to be represented using fewer bits in comparison to floats or other numerical formats.

As used herein, a "precision" refers to a quantity of bits in a bit string that are used for performing computations using the bit string. For example, if each bit in a 16-bit bit string is used in performing computations using the bit string, the bit string can be referred to as having a precision of 16 bits. However, if only 8-bits of a 16-bit bit string are used in performing computations using the bit string (e.g., if the leading 8 bits of the bit string are zeros), the bit string can be referred to as having a precision of 8-bits. As the precision of the bit string is increased, computations can be performed to a higher degree of accuracy. Conversely, as the precision of the bit string is decreased, computations can be performed using to a lower degree of accuracy. For example, an 8-bit bit string can correspond to a data range consisting of two hundred and fifty-five (256) precision steps, while a 16-bit bit string can correspond to a data range consisting of sixty-five thousand five hundred and thirty-six (63,536) precision steps.

As used herein, a "dynamic range" or "dynamic range of data" refers to a ratio between the largest and smallest values available for a bit string having a particular precision associated therewith. For example, the largest numerical value that can be represented by a bit string having a particular precision associated therewith can determine the dynamic range of the data format of the bit string. For a universal number (e.g., a posit) format bit string, the dynamic range can be determined by the numerical value of the exponent bit sub-set of the bit string.

A dynamic range and/or the precision can have a variable range threshold associated therewith. For example, the dynamic range of data can correspond to an application that uses the data and/or various computations that use the data. This may be due to the fact that the dynamic range desired for one application may be different than a dynamic range for a different application, and/or because some computations may require different dynamic ranges of data. Accordingly, embodiments herein can allow for the dynamic range of data to be altered to suit the requirements of disparate applications and/or computations. In contrast to approaches that do not allow for the dynamic range of the data to be manipulated to suit the requirements of different applications and/or computations, embodiments herein can improve resource usage and/or data precision by allowing for the dynamic range of the data to varied based on the application and/or computation for which the data will be used.

FIG. 3 is a functional block diagram in the form of an apparatus including a memory system 304 in accordance with a number of embodiments of the present disclosure. FIG. 3 illustrates a memory system 304, which can be analogous to the memory system 104 illustrated in FIG. 1 and/or the memory system 204 illustrated in FIG. 2, herein. As shown in FIG. 3, the memory system 304 includes a controller 320 (which can be analogous to the controller 120 illustrated in FIG. 1 and/or the controller 220 illustrated in FIG. 2, herein), a DRAM memory device 331 (which can be analogous to one of the memory devices 123, 125 illustrated in FIG. 1 and/or one of the memory devices 223, 225, 227 illustrated in FIG. 2, herein), and a NAND memory device 333 (which can be analogous to one of the memory devices 123, 125 illustrated in FIG. 1 and/or one of the memory devices 223, 225, 227 illustrated in FIG. 2, herein).

As shown in FIG. 3, the NAND memory device 333 can include various portions of memory cells, which can include a set of single level memory cells (SLCs) 335 and a set of multi-level memory cells (MLCs), such as a set of triple-level memory cells (TLCs) 337. In some embodiments, the controller can cause at least a portion of data used by a workload executed on the memory system 304 to be written to the SLC portion 335 and/or or the TLC portion 337 based on the characteristics of the workload involving the data.

For example, data that is classified as hot data can be written to the SLC portion 335 while data that is classified as cold data can be written to the TLC portion 337, or vice versa, as part of optimizing performance of the memory system 304 during execution of a workload. By selectively writing portions of data involved in the workload to different memory portions (e.g., to a SLC portion 335 and/or a TLC portion 337) of the NAND memory device 333, performance of the computing system, especially during execution of workloads described herein, can be improved in comparison to some approaches. Embodiments are not so limited, however, and in some embodiments, hot data can be written to the DRAM memory device, colder data can be written to the NAND memory device 333, and cold data can be written to the emerging memory device 339.

For example, by selectively writing portions of data that correspond to workloads that benefit from rapid executed to the DRAM memory device 331 while writing portions of data that correspond to workloads that may not benefit as much from rapid execution to the SLC portion 335 and/or the TLC portion 337, and/or to the emerging memory device 339, workloads can be allocated to memory devices within the memory system 304 that can allow for optimized execution of the workloads within the memory system 304. Rapidly. For similar reasons, portions of the workloads can be written to an emerging memory device (e.g., the emerging memory device 439 illustrated in FIG. 4, herein).

In some embodiments, at least a portion of the SLC portion 335 of the NAND memory device 333 can be allocated for storage of a look-up table. The look-up table can be a data structure that contains indexing information that can correspond to desired output formats of data written to or from the memory system 304. For example, the look-up table can include pre-fetched information that can be used by the memory system 304 to output various types of data processed by the memory system in a requested format. In some embodiments, the look-up table can facilitate writing of at least a portion of data involved in a workload to one of the memory devices described herein.

FIG. 4 is another functional block diagram in the form of an apparatus including a memory system 404 in accordance with a number of embodiments of the present disclosure. FIG. 4 illustrates a memory system 404, which can be analogous to the memory system 104 illustrated in FIG. 1, the memory system 204 illustrated in FIG. 2, and/or the memory system 304 illustrated in FIG. 3, herein.

As shown in FIG. 4, the memory system 404 includes a controller 420 (which can be analogous to the controller 120 illustrated in FIG. 1, the controller 220 illustrated in FIG. 2, and/or the controller 320 illustrated in FIG. 3, herein), a DRAM memory device 431 (which can be analogous to one of the memory devices 123, 125 illustrated in FIG. 1, one of the memory devices 223, 225, 227 illustrated in FIG. 2, and/or one of the DRAM memory device 331 illustrated in FIG. 3, herein), a NAND memory device 433 (which can be analogous to one of the memory devices 123, 125 illustrated in FIG. 1, one of the memory devices 223, 225, 227 illustrated in FIG. 2, and/or the NAND memory device 333 illustrated in FIG. 3, herein), and an emerging memory device 439 (which can be analogous to one of the memory devices 123, 125 illustrated in FIG. 1 and/or one of the memory devices 223, 225, 227 illustrated in FIG. 2, herein).

The DRAM memory device 431 can include an array of memory cells that include at least one transistor and one capacitor configured to store a charge corresponding to a single data bit. The NAND memory device 433 can include various portions of memory cells, which can include a set of single level memory cells (SLCs) 435 and a set of multi-level memory cells (MLCs), such as a set of triple-level memory cells (TLCs) 437, which can be analogous to the SLC portion 335 and the TLC portion 337, respectively, illustrated and described in connection with FIG. 3, herein.

The emerging memory device 439 can be an emerging memory device, as described above. For example, the emerging memory device 439 can be a resistance variable (e.g., 3-D Crosspoint (3D XP)) memory devices, memory devices that include an array of self-selecting memory (SSM) cells, etc., or any combination thereof.

FIG. 5 is a diagram illustrating a human medical self-diagnostic test subject 540 and a mobile computing device 501 in accordance with a number of embodiments of the present disclosure. As shown in FIG. 5, the mobile computing device 501 includes an imaging device 521, which can be analogous to the imaging device 121 illustrated in FIG. 1, herein and a memory system 504, which can be analogous to the memory system 104, 204, 304, 404 illustrated in FIGS. 1-4, herein. In some embodiments, the mobile computing device 501 can be analogous to the computing system 100 and/or the computing system 200 illustrated in FIGS. 1 and 2, respectively, herein. Embodiments are not so limited, however, and other areas of interest can include a nasal cavity, a stomach, a liver, a kidney, a lung, a brain, a muscle, a joint, a bone, and/or a ligament, among others.

The human medical self-diagnostic test subject 540 can include various areas of interest with respect to performance of medical self-diagnostic testing operations (e.g., the areas of interest 542, 544, 546, and/or 548). The area of interest 542 can be an ear canal or other portion of an ear. The area of interest 544 can be an eyeball or other portion of an eye. The area of interest 546 can be a uterus or womb, and the area of interest 548 can be a genital area that can include one or more testicles.

As shown in FIG. 5, the imaging device 521 can receive information (e.g., images and/or video) related to one or more of the areas of interest 542, 544, 546, 548. The information can be processed and/or analyzed within the mobile computing device 501 for example, using the memory system 504 resident on the mobile computing system 501. In some embodiments, the information (e.g., the images and/or video) can be processed by the mobile computing device 501 as part of performance of a medical self-diagnostic test.

The information, which can include images and/or streaming (e.g., live-streaming) video can be processed by the mobile computing system 501 in connection with execution of one or more applications running on the mobile computing device 501. As described above, execution of such applications can give rise to demanding workloads. Accordingly, as described herein, the information can be selectively written to different memory devices (e.g., the memory devices 223, 225, and/or 227 illustrated in FIG. 2, herein), and therefore different media types (e.g., the media types 224, 226, and/or 228 illustrated in FIG. 2, herein) based on characteristics of the workloads.

In some embodiments, the images and/or video can be processed and/or analyzed by the mobile computing device 501 during execution of an application to analyze the areas of interest 542, 544, 546, and/or 548 illustrated in FIG. 5. In addition, the images and/or video can be processed and/or analyzed by the mobile computing device 501 to detect and/or replace one or more corrupted portions (e.g., pixels) of the images and/or video to recover and/or improve the quality of the images and/or video.

Figure 6:
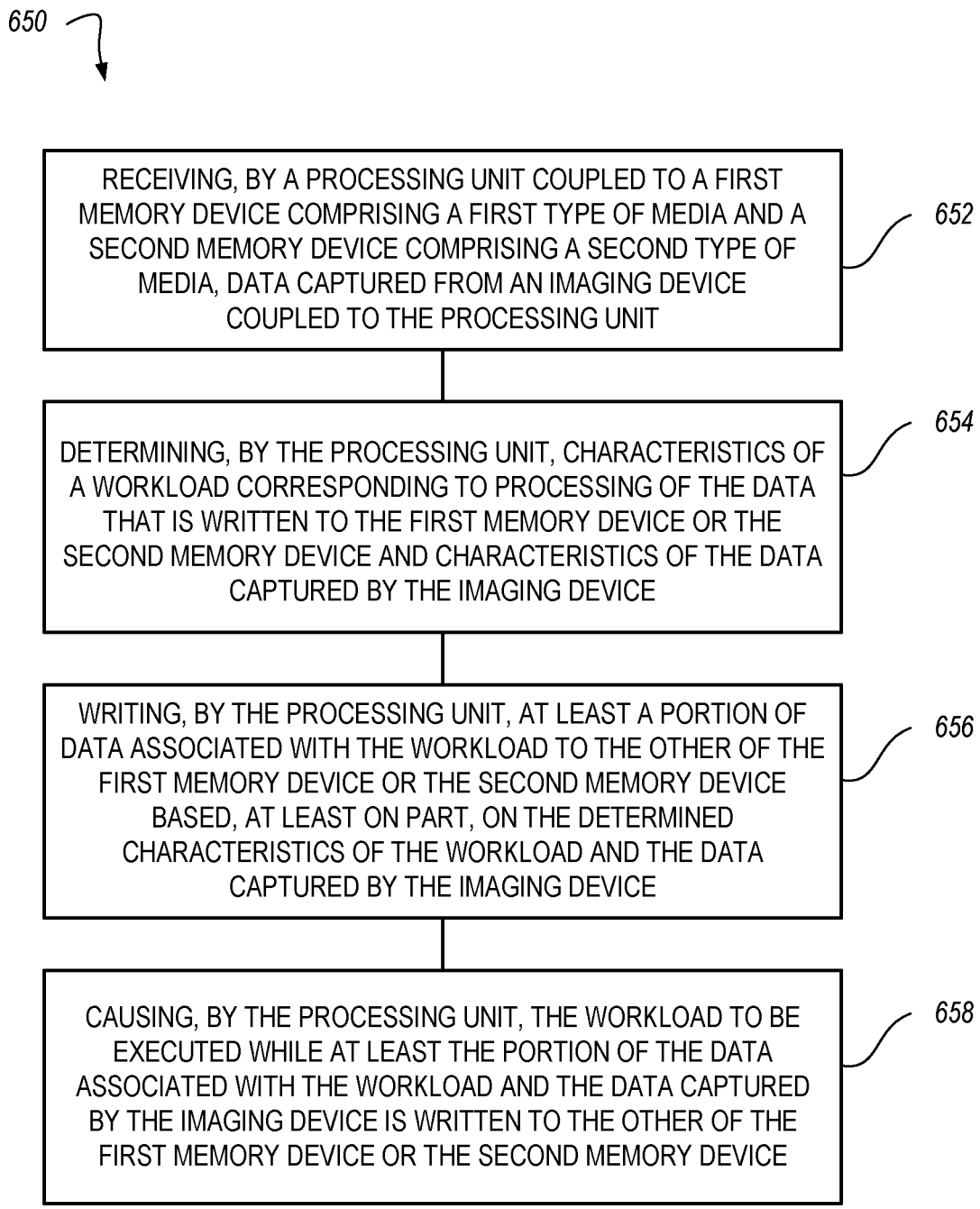
FIG. 6 is a flow diagram representing an example method corresponding to memory system workload allocation in accordance with a number of embodiments of the present disclosure.

FIG. 6 is a flow diagram representing an example method corresponding to memory system workload allocation in accordance with a number of embodiments of the present disclosure. The method 650 can be performed by processing logic that can include hardware (e.g., processing unit(s), processing device(s), control circuitry, dedicated logic, programmable logic, microcode, hardware of a device, and/or integrated circuit(s), etc.), software (e.g., instructions run or executed on a processing unit), or a combination thereof. Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other process flows are possible.

At block 652, the method 650 can include receiving, by processing unit coupled to a first memory device comprising a first type of media and a second memory device comprising a second type of media, data captured from an imaging device coupled to the processing unit. In some embodiments, the characteristics of the workload can include a frequency of access of data associated with the workload during execution of the workload. The first memory device can be analogous to the memory device 123, 223, while the second memory device can be analogous to the memory device 125, 225 illustrated in FIGS. 1 and 2, herein. Further, the first type of media can be analogous to the media type 124, 224, while the second type of media can be analogous to the media type 126, 226 illustrated in FIGS. 1 and 2, herein. The imaging device The imaging device can be analogous to the imaging device 121, 521 illustrated in FIGS. 1 and 5, herein.

At block 654, the method 650 can include determining, by the processing unit, characteristics of a workload corresponding to processing of the data that is written to the first memory device or the second memory device and characteristics of the data captured by the imaging device.

At block, 656, the method 650 can include writing, by the processing unit, at least a portion of data associated with the workload to the other of the first memory device or the second memory device based, at least on part, on the determined characteristics of the workload and the data captured by the imaging device.

At block 658, the method 650 can include causing, by the processing unit, the workload to be executed while at least the portion of the data associated with the workload and the data captured by the imaging device is written to the other of the first memory device or the second memory device.

In some embodiments, the method 650 can include determining, by the processing unit, that the data captured by the imaging device corresponds to performance of an operation to detect an abnormality in at least a portion of a human body. The operation to detect the abnormality in the body can be performed as part of a self-diagnostic medical test. In such embodiments, the method 650 can further include writing at least the portion of the data associated with the workload and the data captured by the imaging device to the other of the first memory device or the second memory device based, at least in part, on determining that the workload or the data captured by the imaging device, or both, corresponds to performance of the operation to detect the abnormality in at least the portion of the human body.

The method 650 can further include determining, by the processing unit, that the data captured by the imaging device corresponds to performance of an ultrasound imaging operation and writing at least the portion of the data associated with the workload and the data captured by the imaging device to the other of the first memory device or the second memory device based, at least in part, on determining that the workload or the data captured by the imaging device, or both corresponds to performance of the ultrasound imaging operation.

The method 650 can further include determining, by the processing unit, that the workload corresponds to performance of an operation to process an image or a video stream and writing at least the portion of the data associated with the workload to the other of the first memory device or the second memory device based, at least in part, on determining that the workload corresponds to performance of the operation to process the image or the video stream. In such embodiments, the method 650 can further include performing, by the processing unit, the operation to process the image or the video stream by exchanging at least one pixel of the image or the video stream, correcting a blurred portion of the image or the video stream, and/or removing noise from the image or the video stream.

As described above, the first memory device or the second memory device can be a non-persistent memory device, and the other of the first memory device or the second memory device can be a persistent memory device. In some embodiments, the processing unit, the first memory device, and the second memory device can be resident on a mobile computing device (e.g., the mobile computing device 501 illustrated in FIG. 5, herein). In such embodiments, the method 650 can include determining, writing, and causing, by the processing unit in the absence of control signals generated external to the mobile computing device. Embodiments are not so limited, and in some embodiments, the method 650 can include writing at least the portion of data associated with the workload to the other of the first memory device or the second memory device as part of an operation to optimize battery consumption of the mobile computing device.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method, comprising:
    receiving, by a processing unit coupled to a first memory device comprising a first type of media and a second memory device comprising a second type of media, data captured from an imaging device coupled to the processing unit;
    storing the data with the first memory device or the second memory device;
    executing, by the processing unit while the data is stored with the first memory device or the second memory device, a workload corresponding to processing of the data that is received by the first memory device or the second memory device;
    determining, by the processing unit, during execution of the workload, characteristics of the workload and characteristics of the data captured by the imaging device;
    writing, by the processing unit, at least a portion of data associated with the workload to the other of the first memory device or the second memory device based, at least in part, on the determined characteristics of the workload and the data captured by the imaging device; and
    causing, by the processing unit, an application using at least the portion of the data associated with the workload to be executed while at least a different portion of the data associated with the workload and the data captured by the imaging device is written to the other of the first memory device or the second memory device.

2. The method of claim 1, wherein the characteristics of the workload comprise a frequency of access of data associated with the workload during execution of the workload.

3. The method of claim 1, further comprising:
    determining, by the processing unit, that the data captured by the imaging device corresponds to performance of an operation to detect an abnormality in at least a portion of a human body; and
    writing at least the portion of the data associated with the workload and the data captured by the imaging device to the other of the first memory device or the second memory device based, at least in part, on determining that the workload or the data captured by the imaging device, or both, corresponds to performance of the operation to detect the abnormality in at least the portion of the human body.

4. The method of claim 1, further comprising:
    determining, by the processing unit, that the data captured by the imaging device corresponds to performance of an ultrasound imaging operation; and
    writing at least the portion of the data associated with the workload and the data captured by the imaging device to the other of the first memory device or the second memory device based, at least in part, on determining that the workload or the data captured by the imaging device, or both corresponds to performance of the ultrasound imaging operation.

5. The method of claim 1, further comprising:
determining, by the processing unit, that the workload corresponds to performance of an operation to process an image or a video stream;
writing at least the portion of the data associated with the workload to the other of the first memory device or the second memory device based, at least in part, on determining that the workload corresponds to performance of the operation to process the image or the video stream; and
performing, by the processing unit, the operation to process the image or the video stream by exchanging at least one pixel of the image or the video stream, correcting a blurred portion of the image or the video stream, or removing noise from the image or the video stream, or any combination thereof.

6. The method of claim 1, wherein the first memory device or the second memory device is a non-persistent memory device, and wherein the other of the first memory device or the second memory device is a persistent memory device.

7. The method of claim 1, wherein the processing unit, the first memory device, and the second memory device are resident on a mobile computing device, and wherein the method comprises performing the operations of determining, writing, and causing, by the processing unit in the absence of control signals generated external to the mobile computing device.

8. The method of claim 1, wherein the processing unit, the first memory device, and the second memory device are resident on a mobile computing device, and wherein the method comprises writing at least the portion of data associated with the workload to the other of the first memory device or the second memory device as part of an operation to optimize battery consumption of the mobile computing device.

9. An apparatus, comprising:
a first memory device comprising a first type of media;
a second memory device comprising a second type of media; and
a processing unit coupled to the first memory device and the second memory device, wherein the processing unit is to:
receive information captured by an imaging device couplable to the processing unit;
store the data with the first memory device or the second memory device;
execute an operation to process the received information captured by the imaging device, wherein the operation to process received information captured by the imaging device has a particular workload corresponding thereto;
execute the workload while the received information is stored by the first memory device or the second memory device;
determine characteristics of the workload when the information captured by the imaging device is written to the first memory device or the second memory device, wherein the characteristics of the workload include at least one of an access frequency of data associated with the information captured by the imaging device, a latency associated with execution of an application to process the information captured by the imaging device, or an amount of processing resources consumed in execution of the application, or any combination thereof;
determine, based on the characteristics of the workload, during execution of the workload, whether to write at least a portion of data associated with the workload to the other of the first memory device or the second memory device; and
control allocation of execution of the application using at least the portion of the data that is written to the other of the first memory device or the second memory device such that at least the portion of the application is subsequently executed after at least the portion of the data has been written to the other of the first memory device or the second memory device.

10. The apparatus of claim 9, wherein the processing unit is to:
determine that the workload corresponds to performance of an ultrasound imaging operation;
receive, from the imaging device, information that corresponds to the ultrasound imaging operation; and
write the information that corresponds to the ultrasound imaging operation to the first memory device or the second memory device based, at least in part on the determination that the workload corresponds to performance of the ultrasound imaging operation.

11. The apparatus of claim 9, wherein the processing unit is to:
determine that the workload corresponds to performance of an operation to detect an abnormality in at least one of an eyeball, an ear, a nose, or a testicle, or any combination thereof;
receive, from the imaging device, information that corresponds to the detected abnormality in at least the one the eyeball, the ear, the nose, or the testicle, or any combination thereof; and
write at least the portion of the data associated with the workload to the other of the first memory device or the second memory device based, at least in part, on the determination that the workload corresponds to performance of the operation to detect the abnormality in at least one of the eyeball, the ear, the nose, or the testicle, or any combination thereof.

12. The apparatus of claim 9, wherein the processing unit is to:
determine that the workload corresponds to performance of an operation to process an image or a video received from the imaging device;
write at least the portion of the data associated with the workload to the other of the first memory device or the second memory device based, at least in part, on the determination that the workload corresponds to performance of the operation to process the image or the video received from the imaging device; and
cause performance of the operation to process the image or the video by replacing at least one pixel of the image or the video, correcting a blurred portion of the image or the video, or removing noise from the image or the video, or any combination thereof.

13. The apparatus of claim 9, wherein the first type of memory or the second type of memory, or both, comprises sets of memory cells that exhibit different storage characteristics.

14. The apparatus of claim 9, wherein the first memory device or the second memory device is a non-persistent memory device, and wherein the other of the first memory device or the second memory device is a persistent memory device.

15. The apparatus of claim 9, wherein the first memory device or the second memory device is a NAND flash memory device that comprises a set of single level memory cells (SLCs) and a set of multi-level memory cells (MLCs); and
wherein the processing unit is to write at least the portion of the data associated with the workload to the set of SLC memory cells or the set of MLC memory cells based, at least in part, on the characteristics of the workload.

16. The apparatus of claim 15, wherein the set of SLCs are configured to store a look-up table to facilitate writing of at least the portion of the data to the other of the first memory device or the second memory device.

17. The apparatus of claim 9, wherein the first memory device, the second memory device, and the processing unit are resident on a smartphone.

18. A system, comprising:
a memory system comprising a processing unit, a first memory device comprising a first type of media, a second memory device comprising a second type of media, and a third memory device comprising a third type of media; and
an imaging device coupled to the first memory device the second memory device, and the third memory device, wherein the processing unit is to:
receive signaling comprising information captured by the imaging device;
store the information with the first memory device, the second memory device, or the third memory device;
execute, using data written to the first memory device, the second memory device, or the third memory device, an application that includes processing the information detected by the imaging device;
determine characteristics of a workload based on the executed application while the data is written to the first memory device, the second memory device, or the third memory device; and
write at least a portion of data associated with the workload to at least one of the other of the first memory device, the second memory device, or the third memory device during execution of the workload based, at least in part, on the determined characteristics of the workload and the information detected by the imaging device.

19. The system of claim 18, wherein the first memory device is a dynamic random-access memory device, the second memory device is a NAND flash memory device, and the third memory device is a three-dimensional crosspoint memory device.

20. The system of claim 18, wherein:
the first media type comprises an array of memory cells that include at least one capacitor and at least one transistor,
the second media type comprises an array of floating-gate metal-oxide-semiconductor field-effect transistors, and
the third type of media comprises an array of resistance variable memory cells that are configured to perform bit storage based on a change in a bulk resistance associated with the resistance variable memory cells.

21. The system of claim 18, wherein the memory system and the imaging device are resident on a mobile computing device.

22. The system of claim 21, wherein the processing unit is to write at least the portion of data associated with the workload to at the least one of the other of the first memory device, the second memory device, or the third memory device to optimize battery consumption of the mobile computing device as part of execution of the workload that includes processing the information detected by the imaging device.

23. The system of claim 18, wherein the memory system and the imaging device are resident on a mobile computing device, and wherein the processing unit is to:
receive data captured by the imaging device in conjunction with performance of a medical self-diagnostic test;
write at least a portion of the data captured by the imaging device to at least one of the other of the first memory device, the second memory device, or the third memory device based, at least in part, on a determined category associated with the medical self-diagnostic test; and
execute, using at least the portion of the data captured by the imaging device written to the first memory device, the second memory device, or the third memory device, a workload that includes at least the portion of the data captured by the imaging device.

24. The system of claim 18, wherein the processing unit is to:
determine the characteristics of the executed workload while the data is written to the first memory device, the second memory device, or the third memory device by monitoring at least one of an access frequency of data associated with the workload, a latency associated with execution of the workload, or an amount of processing resources consumed in execution of the workload, or any combination thereof; and
write at least the portion of data associated with the workload to at least one of the other of the first memory device, the second memory device, or the third memory device based, at least in part, on the determined access frequency of data associated with the workload, the latency associated with execution of the workload, or the amount of processing resources consumed in execution of the workload, or any combination thereof.

25. The system of claim 18, wherein at least a portion of the data written to the first memory device, the second memory device, or the third memory device is formatted according to a universal number format.

* * * * *